United States Patent
Evans et al.

(10) Patent No.: US 10,571,400 B2
(45) Date of Patent: Feb. 25, 2020

(54) PLASMONIC NANOPARTICLE IMMUNOASSAY METHOD

(71) Applicant: The General Hospital Corporation, Boston, MA (US)

(72) Inventors: Conor L. Evans, Charlestown, MA (US); W. Peter Hansen, Drury, MA (US); Robert A. Hoffman, Livermore, CA (US); Petra B. Krauledat, Drury, MA (US); Daniel W. Cramer, Chestnut Hill, MA (US)

(73) Assignee: The General Hospital Corporation, Boston, MA (US)

( * ) Notice: Subject to any disclaimer, the term of this patent is extended or adjusted under 35 U.S.C. 154(b) by 108 days.

(21) Appl. No.: 15/556,998

(22) PCT Filed: Mar. 11, 2016

(86) PCT No.: PCT/US2016/022066
§ 371 (c)(1),
(2) Date: Sep. 8, 2017

(87) PCT Pub. No.: WO2016/145342
PCT Pub. Date: Sep. 15, 2016

(65) Prior Publication Data
US 2018/0067049 A1    Mar. 8, 2018

Related U.S. Application Data

(60) Provisional application No. 62/131,382, filed on Mar. 11, 2015.

(51) Int. Cl.
*G01N 21/64* (2006.01)
*G01N 15/14* (2006.01)
(Continued)

(52) U.S. Cl.
CPC ......... *G01N 21/648* (2013.01); *C12N 5/0694* (2013.01); *G01N 15/1459* (2013.01);
(Continued)

(58) Field of Classification Search
CPC ............ A61K 31/7088; A61K 31/7105; A61K 31/713; A61K 45/06; C12N 15/113;
(Continued)

(56) References Cited

U.S. PATENT DOCUMENTS 5,776,785 A  *  7/1998  Lin ..................... G01N 21/648
                                                        435/6.1
6,530,944 B2     3/2003  West et al.
(Continued)

FOREIGN PATENT DOCUMENTS

WO    2006122222 A2    11/2006
WO    2011046807 A2    4/2011

OTHER PUBLICATIONS

Crow et al., Plasmonic Flow Cytometry by Immunolabeled Nanorods, Cytometry Part A, 79A: 57-65, 2011. (Year: 2011).*
(Continued)

*Primary Examiner* — Jennifer Wecker
(74) *Attorney, Agent, or Firm* — Quarles & Brady LLP (57) ABSTRACT

A method for detecting a target cell surface molecule and classifying cell types in a fluid sample. The method involves the addition of a reagent to the fluid sample. The reagent includes nanoparticles with optical plasmonic resonances, and at least one fluorescent probe. The nanoparticles are a bio-optical probe for the target cell surface molecule. Each fluorescent probe targets a cell classification marker. The method further involves the acquisition of an image using dark field microscopy and fluorescence microscopy to detect and quantify the presence or absence of any cells in the fluid sample having the target cell surface molecule or having the cell classification marker.

34 Claims, 10 Drawing Sheets

(51) Int. Cl.

| | |
|---|---|
| *G01N 33/58* | (2006.01) |
| *G01N 33/543* | (2006.01) |
| *C12N 5/09* | (2010.01) |
| *G01N 33/569* | (2006.01) |
| *C12N 5/0784* | (2010.01) |
| *A61K 31/7088* | (2006.01) |
| *A61K 31/7105* | (2006.01) |
| *C12N 15/113* | (2010.01) |
| *A61K 31/713* | (2006.01) |
| *G01N 15/00* | (2006.01) |

(52) U.S. Cl.
CPC ..... *G01N 21/6456* (2013.01); *G01N 33/54346* (2013.01); *G01N 33/54373* (2013.01); *G01N 33/56972* (2013.01); *G01N 33/582* (2013.01); *G01N 33/585* (2013.01); *A61K 31/7088* (2013.01); *A61K 31/713* (2013.01); *A61K 31/7105* (2013.01); *C12N 5/064* (2013.01); *C12N 15/113* (2013.01); *C12N 2310/113* (2013.01); *C12N 2310/141* (2013.01); *G01N 2015/008* (2013.01); *G01N 2015/1486* (2013.01); *G01N 2333/4725* (2013.01)

(58) Field of Classification Search
CPC ........ C12N 2310/113; C12N 2310/141; C12N 2320/30; C12N 5/0694; G01N 15/1459; G01N 2015/008; G01N 2015/1486; G01N 21/6456; G01N 21/648; G01N 2333/4725; G01N 33/54346; G01N 33/54373; G01N 33/56972; G01N 33/582; G01N 33/585
See application file for complete search history.

(56) References Cited

U.S. PATENT DOCUMENTS

| | | | |
|---|---|---|---|
| 7,137,815 | B2 | 11/2006 | Matsutani et al. |
| 8,889,362 | B2 | 11/2014 | Hansen |
| 2004/0246480 | A1 | 12/2004 | Hansen et al. |
| 2005/0053974 | A1* | 3/2005 | Lakowicz .......... G01N 21/4788 435/6.12 |
| 2009/0148863 | A1* | 6/2009 | Xu .................. G01N 33/54346 435/7.1 |
| 2009/0326614 | A1 | 12/2009 | El-Sayed et al. |
| 2013/0172207 | A1* | 7/2013 | Dai ...................... G01N 33/553 506/9 |
| 2014/0106469 | A1* | 4/2014 | Wu .................. G01N 33/54346 436/501 |
| 2014/0220580 | A1* | 8/2014 | Brown ............. G01N 33/57434 435/6.12 |
| 2014/0227182 | A1 | 8/2014 | Pomper et al. |

OTHER PUBLICATIONS

Korb, et al., Sensitive in Situ Hybridization and Immunohistological Detection Using Resonance Light Scattering (RLS) Particles, Copyright Genicon Sciences Corporation 2002, 1 page.
MacLaughlin, et al., Evaluation of SERS Labeling of CD20 on CLL Cells Using Optical Microscopy and Fluorescence Flow Cytometry, Nanomedicine: Nanotechnology, Biology and Medicine, 2013, 9(1):55-64.
Zucker, et al., Detection of TiO2 Nanoparticles in Cells by Flow Cytometry, Cytometry Part A, 2010, 77A:677-685.
European Patent Office, Extended European Search Report, Application No. 16762620.9, dated Dec. 12, 2018, 10 pages.
BD Biosciences, Technical Bulletin, an Introduction to Compensation for Multicolor Assays on Digital Flow Cytometers, Aug. 2009, 12 pages.
Bohren, et al., Chapter 12. Surface Modes in Small Particles, Absorption and Scattering of Light by Small Particles, a Wiley-Interscience Publication, John Wiley & Sons, 1983, pp. 325-380.
Felder, et al., MUC16 (CA125): Tumor Biomarker to Cancer Therapy, a Work in Progress, Molecular Cancer, 2014, 13:129, 15 pages.
Hansen, et al., Physics of a Rapid CD4 Lymphocyte Count with Colloidal Gold, Cytometry Part A, 2012, 81A:222-231.
Hong, et al., Scaling Law for the Radius of Gyration of Proteins and Its Dependence on Hydrophobicity, Journal of Polymer Science: Part B: Polymer Physics, 2009, 47:207-214.
Patankar, et al., Potent Suppression of Natural Killer Cell Response Mediated by the Ovarian Tumor Marker CA125, Gynecologic Oncology, 2005, 99(3):704-713.
Yguerabide, et al., Light-Scattering Submicroscopic Particles as Highly Fluorescent Analogs and Their Use as Tracer Labels in Clinical and Biological Applications: II. Experimental Characterization, Analytical Biochemistry, 1998, 262(2):157-176.
Yu, et al., Identity Profiling of Cell Surface Markers by Multiplex Gold Nanorod Probes, Nano Letters, 2007, 7(8):2300-2306.
Zola, High-Sensitivity Immunofluorescence/Flow Cytometry: Detection of Cytokine Receptors and Other Low-Abundance Membrane Molecules, Current Protocols in Cytometry, 2004, 30(1):6.3.1-6.3.13.
International Search Report and Written Opinion for international application No. PCT/US2016/022066 dated Jun. 3, 2016, 14 pages.
Crow et al., Plasmonic Flow Cytometry by Immunolabeled Nanorods, Cytometry Part A, 79A: 57-65, 2011, 9 pages.

* cited by examiner

PLASMONIC NANOPARTICLE IMMUNOASSAY METHOD

CROSS-REFERENCE TO RELATED APPLICATIONS

This application represents the U.S. National Stage of International Application No. PCT/US2016/022066, filed Mar. 11, 2016 which claims priority to U.S. Patent Application No. 62/131,382 filed Mar. 11, 2015.

STATEMENT REGARDING FEDERALLY SPONSORED RESEARCH

Not Applicable.

BACKGROUND OF THE INVENTION

1. Field of the Invention

This invention relates to methods for classifying cell types in a fluid sample and detecting and quantifying target cell surface molecules using a reagent. The reagent includes at least one fluorescent probe and nanoparticles. Each fluorescent probe targets a cell classification marker. The nanoparticles are a bio-optical probe for the target cell surface molecule. The method further involves the use of one or multiple fluorescent probes to identify cells of a particular class and dark field microscopy to quantify the target cell surface molecule.

2. Description of the Related Art

There are new requirements within the field of cellular immunology for not only high sensitivity detection of rare cell surface antigens, receptors and other surface molecules, but also the simultaneous identification of the cell subclass to which such a rare surface moiety is bound or on which it is expressed. For example, cytokine receptors are generally expressed at low density on the cell surface and their specific action depends on whether expression is on pluri-potent stem cells, macrophages, monocytes or dendritic cells (Heddy Zola, *Current Protocols in Cytometry* (2004) 6.3.1-6.3.13, C 2004 by John Wiley & Sons, Inc.). In another example, the mucin molecule MUC16 (CA125) has been shown to bind at very low levels to several leukocyte subclasses. When bound to the leukocyte subclass termed "Natural Killer (NK) Cells" it causes an "immune escape mechanism" for epithelial ovarian cancer (EOC) to be activated (Patankar et al., "Potent suppression of natural killer cell response mediated by the ovarian tumor marker CA125", *Gynecol Oncol.* 2005; 99(3):704-713). Detecting low-level surface MUC16 and simultaneously knowing that it was bound to an NK cell is therefore significant.

There are fundamental physical barriers within fluorescence technology that prevent using fluorescent markers for rare surface antigens while other fluorescent immunophenotyping markers are simultaneously used to identify cell types or lineage. Immunophenotyping uses multiple fluorescent antibody probes, each with a unique fluorophore, and Boolean logic to identify cell subsets. For example, the T-Helper subset of lymphocytes can be immunophenotyped in principle by simultaneously labeling blood cells with anti-CD45 (pan leukocytes), anti-CD3 (pan mature T-cells), and anti-CD4 (Helper T-Cells and all Monocytes). In practice, while each of these antibodies carries a unique fluorophore, the emission spectra of the fluorophores inevitably overlap and defeat simple Boolean strategies for classifying the cell. A linear algebra method termed "color compensation" can be used to subtract overlap from multiple emission spectra and correctly classify the cell type provided the intensities of the multiple fluorescence signals are approximately equal. The common markers used to identify cell type have been chosen to meet this critical equal emission intensity restriction or "rule". The fluorescence signal from a rare surface antigen is, by definition, weak by orders of magnitude compared to immunophenotyping markers, meaning that color compensation for the weak marker will fail. This failure is present even when the very bright fluorescence labels such as phycoerythrin (PE) and Brilliant Violet (BV) are used to detect rare antigens. A BD Biosciences Technical Bulletin (August, 2009) entitled, *An Introduction to Compensation for Multicolor Assays on Digital Flow Cytometers* implies that the problem of spectral overlap in the presence of signal inequality cannot be solved. It states: "[e]ven with proper compensation, if a large amount of unwanted signal spills over into a neighboring band where a dim signal is to be detected, resolution sensitivity might be lowered and populations might not be accurately resolved".

Therefore, what is needed is a method and apparatus combination that enables the detection of low-density cell surface antigens in the presence of high levels of spectral spillover from an unlimited number immunophenotyping fluorophores without color compensation for the rare antigen.

SUMMARY OF THE INVENTION

The present invention describes a novel bio-optical method and apparatus combination that enables the detection of low-density cell surface antigens in the presence of high levels of spectral spillover from an unlimited number immunophenotyping fluorophores without color compensation for the rare antigen. For example, the method can be used to detect and quantify the rare surface binding of MUC16 molecules on specific leukocyte subsets. In the case of MUC16 the detection sensitivity of the present invention approaches that of single molecules, which enables not only detection, but also quantification of this rare surface molecule.

The present invention provides a method and apparatus that uses nanoparticles with visible and near-infrared (optical) plasmonic resonances as quantitative bio-optical probes for rare cell surface antigens in combination with dark field and fluorescence microscope optics in the presence of fluorescent lineage probes to identify the cell type. By replacing fluorescence detection with a combination of dark field microscopy, fluorescence microscopy, and plasmonic nanoparticle surface antigen probes, the present invention corrects the failure of color compensation when the surface antigen is rare and subject to high levels of spillover of emitted light from inherently bright lineage probes.

The present invention makes use of the intense light-scatter-based spectral radiance per unit area of a plasmonic nanoparticle (PNP) or cluster of plasmonic nanoparticles. This light-scatter-based spectral radiance of a plasmonic nanoparticle can exceed that of a fluorophore by $10^5$ to $10^6$ fold (Bohren et al., "Surface Modes in Small Particles in Absorption and Scattering of Light by Small Particles" Weinheim W-VVG; 2004). Plasmonic nanoparticles, such as gold sols, can be conjugated to antibodies that bind with high specificity for cell surface antigens (see, U.S. Pat. No. 8,889,362 to Hansen; and Hansen et al., "Physics of a rapid CD4 lymphocyte count with colloidal gold", *Cytometry Part A*. 2012; 81A: 222). When observed by dark field microscopy, in which contrast arises due to light scattering in a sample rather than transmission properties of the sample, these bound particles appear as spatially punctate, intense, light sources against a dark background that are far brighter than nuclear membrane or cytoplasmic light scattering. When the particle diameters are smaller than the diffraction limit of the dark field light microscope (e.g., less than approximately 1 micron), the punctate light sources appear as individual Airy discs of intense light emission, well above the light scatter background caused by other natural features of single cells. These bright Airy discs are readily detected by digital color photography with sub-second exposure times.

When fluorescent lineage markers are used simultaneously to identify the cells type, their fluorescence emission is many orders of magnitude weaker than that caused by the nanoparticle label light scatter and contribute no light scattering signal themselves. Thus lineage marker fluorescence is non-interfering with bound plasmonic nanoparticle light scatter under dark field. We have shown that following the methods of the present invention, the plasmonic nanoparticles themselves do not quench the lineage marker fluorescence. Quenching occurs when fluorophores are near (<1 nanometer) the surface of a plasmonic nanoparticle. By using protein spacers, such as IgG antibodies to coat plasmonic nanoparticles, a physical spacer of approximately 15 nanometers (nm) prevents the approach of fluorophores and thus avoids fluorescence quenching.

Unlike systems that use fluorescence alone, a plasmonic nanoparticle probe for a rare antigen can exhibit spectral emission completely within lineage marker fluorescent emission bands and be readily detected without color compensation. This robust property of plasmonic nanoparticles further elucidates how the long-standing problem of spectral spillover masking the detection of rare antigens by conventional fluorescence microscopy and flow cytometry is solved by the present invention.

Punctate light sources caused by plasmonic nanoparticles (PNPs) not only make it possible to detect rare cell surface antigens, but also, for the first time make it possible to quantify their surface abundance. The punctate light sources of individual plasmonic nanoparticle can be photographed and counted by manual or automated image analysis methods, thus enabling quantification of rare surface antigens. Example applications of this aspect of the present invention include the plasmonic nanoparticle detection of low antigen density cancer-associated mucins on the surface of fluorescently identified leukocyte subsets. Mathematical models of the cancer mucin, MUC16 indicate that single punctate sources of high contrast light correspond to single MUC16 molecules. Using various analytical and mathematical techniques, the physical size of intact MUC16 is of the order of 1 micron (see, Felder et al., "MUC16 (CA125): Tumor Biomarker to Cancer Therapy, A Work in Progress", *Molecular Cancer* 2014 13:129; and L. Hong and J. Lei., "Scaling Law for the Radius of Gyration of proteins and its Dependency on Hydrophobicity", *J. Polymer Science* Volume 47, Issue 2 15 Jan. 2009 pp 207-214). Peripheral blood cells such as lymphocytes and natural killer cells, have surface areas of approximately 300 square microns, indicating that the maximum number of intact MUC16 molecules bound to the surface of such cells cannot exceed approximately 300. Within each MUC16 mucin are 60 tandem repeat epitopes for the 156 amino acid antigen CA125. Each epitope has a physical size of approximately 20 nm. Under the extreme assumption that all 60 epitopes were present as a linear string, the total binding domain would also be of the order of 1 micron in length. If, for example, 80 nm plasmonic nanoparticles were conjugated to anti CA125 antibodies, all would bind within a zone with a linear dimension of approximately 1 micron. A zone of this size lies at the approximate diffraction limit for practical dark field visible light microscopy. Consequently, the multiple 80 nm plasmonic nanoparticles that can bind to one intact MUC16 molecule will appear as a single bright Airy disk with dark field microscopy. In this example, one Airy disk corresponds to one MUC16 molecule. Using the methods and apparatus of this invention, weak binding to the absolute lower limit of single MUC 16 molecules quantified on the surface of cells by counting Airy disks in the presence of multiple fluorescent lineage markers. Thus, solving the impasse of failed color compensation when expression or surface binding levels are vastly unequal, as is the case with rare or low level antigens in the presence of lineage marking antigens.

Gold plasmonic nanoparticles are used as the specific examples that describe the present invention. The invention is not limited to this nanoparticle, but includes any plasmonic nanoparticle composition that is detectable by dark field microscopy.

One aspect of the invention provides a method for detecting a target cell surface molecule and classifying cell types in a fluid sample. The method involves the addition of a reagent to the fluid sample. The reagent includes nanoparticles with optical plasmonic resonances, and at least one fluorescent probe. The nanoparticles are a bio-optical probe for the target cell surface molecule. Each fluorescent probe targets a cell classification marker. The method further involves the acquisition of an image using dark field microscopy and fluorescence microscopy to detect and quantify the presence or absence of any cells in the fluid sample having the target cell surface molecule or having the cell classification marker.

Another aspect of the invention provides a reagent for detecting a target cell surface molecule and classifying cell types in a fluid sample. The reagent includes: (i) nanoparticles with optical plasmonic resonances, wherein the nanoparticles are a bio-optical probe for the target cell surface molecule; and (ii) at least one fluorescent probe, wherein each fluorescent probe targets a cell classification marker.

Another aspect of the invention provides a method for detecting a target cell surface molecule in a fluid sample. The method includes the steps of (a) dispersing nanoparticles with optical plasmonic resonances in the fluid sample, wherein the nanoparticles are a bio-optical probe for the target cell surface molecule; (b) thereafter adding a nanoparticle coagulating agent to the fluid sample; (c) acquiring an image using dark field microscopy to detect and quantify the presence or absence of any cells in the fluid sample having the target cell surface molecule.

This aspect of the invention is advantageous over other methods that teach that a blood sample, PNPs and a coagulating agent (e.g., hexadimethrine bromide, SigmaAldrich) are combined simultaneously for speed of testing. In one non-limiting embodiment of the present invention, a blood sample and PNPs are combined and mixed in a first step to enhance the homogeneous dispersal of monomeric PNPs within the blood sample before hexadimethrine bromide is added. In this embodiment of the invention, the coagulating agent is combined in a second later step after pockets of high concentration PNPs are dispersed in the blood sample in a first combining and mixing step. By separating these steps, and not combining blood, PNPs and the coagulating agent simultaneously, the present method avoids undue clumping of PNPs by the coagulating agent, which is an inhibitor to PNP labeling of blood cells.

These and other features, aspects, and advantages of the present invention will become better understood upon consideration of the following detailed description, drawings and appended claims.

DETAILED DESCRIPTION OF THE INVENTION

The invention provides a method for detecting a target cell surface molecule and classifying cell types in a fluid sample. The method includes adding a reagent to the fluid sample. The reagent includes nanoparticles with optical plasmonic resonances and at least one fluorescent probe. The nanoparticles are a bio-optical probe for the target cell surface molecule. Each fluorescent probe targets a cell classification marker. The method also includes acquiring an image using dark field microscopy and fluorescence microscopy to detect and quantify the presence or absence of any cells in the fluid sample having the target cell surface molecule and quantifying the target cell surface molecule on a cell-by-cell basis. The acquired image is also used to detect and quantify the presence or absence of any cells in the fluid sample having the cell classification marker.

In one embodiment the target cell can be a leukocyte. The target cell surface molecule can be a rare cell surface antigen. A non-limiting example of the target cell surface molecule is the mucin molecule MUC16.

The nanoparticles can be plasmonic nanoparticles detectable by dark field microscopy. The at least one fluorescent probe can be detectable by fluorescence microscopy. The nanoparticles can be silver, gold, nickel, copper, titanium, silicon, gadolinium, palladium, platinum, or chromium. The nanoparticles can be gold sols. The nanoparticles can be 10-200 nanometers or 40-80 nanometers in size. The nanoparticles can be conjugated with antibodies or antibody complexes and the antibodies can bind with specificity for cell surface antigens. The nanoparticles can be conjugated with anti-MUC16 monoclonal antibodies.

Any of the fluorescent probes can be a fluorophore. Non-limiting example fluorescent probes include Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 635, Alexa Fluor 660, Alexa Fluor 680), Cascade Blue, Cascade Yellow and R-phycoerythrin, FITC, Rhodamine, and Texas Red, Cy5, Cy5.5, Cy7. The fluorescent probe can have an absorption maximum between 490-500 nm, an emission maximum between 510-530 nm, and an emission color of green. The fluorescent probe can be R-phycoerythrin. The at least one fluorescent probe can have an absorption maximum between 630-640 nm, an emission maximum between 640-650 nm, and an emission color of far-red.

The nanoparticles can create intense light scatter based spectral radiance per unit area. The intense light scatter based spectral radiance can exceed the spectral radiance of a fluorophore by $10^5$ to $10^6$. The fluorescent probe can have a fluorescence emission one or more orders of magnitude weaker than that caused by the nanoparticles light scatter thereby not interfering with the nanoparticle light scatter.

The nanoparticles can appear as spatially punctate, intense light sources in the acquired image. The punctate light sources can appear as individual Airy discs of intense light emission in the acquired image such that the Airy discs are readily detectable in the acquired image. The nanoparticles can be coated with protein spacers. The protein spacers can provide a physical spacer of 1 to 100 nanometers, or 5 or 50 nanometers, or 10 to 20 nanometers, prevents the approach of fluorophores and avoids fluorescence quenching. The protein spacers can comprise IgG antibodies.

The detection and quantification of the presence or absence of any cells in the fluid sample having the target cell surface molecule and detection of the presence or absence of any cells in the fluid sample having the cell classification marker can be done manually or using automated image analysis.

The method can further include stepping a focal plane of an objective of a dark field microscope through at least one labeled cell in the fluid sample that has the target cell surface molecule and enumerating in-focus plasmonic nanoparticles on the least one labeled cell.

Non-limiting examples of the acquired image can be a dark field microscopy image or an acquired image using flow cytometry.

The invention also provides a reagent for detecting a target cell surface molecule and classifying cell types in a fluid sample. The reagent includes nanoparticles with visible light plasmonic resonances and at least one fluorescent probe. The nanoparticles can be a bio-optical probe for the target cell surface molecule. Each fluorescent probe targets a cell classification marker. The nanoparticles can be plasmonic nanoparticles detectable by dark field microscopy. The nanoparticles can be silver, gold, nickel, copper, titanium, silicon, gadolinium, palladium, platinum, or chromium. The nanoparticles can be gold sols. The nanoparticles can be 10-200 nanometers in size. The nanoparticles can be 10-100 nanometers in size. The nanoparticles can be 40-80 nanometers in size.

The nanoparticles can be conjugated with antibodies, or antibody complexes, and the antibodies can bind with specificity for cell surface antigens. The nanoparticles can be conjugated with anti-MUC16 monoclonal antibodies.

Any of the fluorescent probes can be a fluorophore. Non-limiting example fluorescent probes include Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 635, Alexa Fluor 660, Alexa Fluor 680), Cascade Blue, Cascade Yellow and R-phycoerythrin, FITC, Rhodamine, and Texas Red, Cy5, Cy5.5, Cy7. The fluorescent probe can have an absorption maximum between 490-500 nm, an emission maximum between 510-530 nm, and an emission color of green. The at least one fluorescent probe can be R-phycoerythrin. The fluorescent probe can have an absorption maximum between 630-640 nm, an emission maximum between 640-650 nm, and an emission color of far-red.

The invention also provides a method for detecting a target cell surface molecule in a fluid sample. The method includes dispersing nanoparticles with optical plasmonic resonances in the fluid sample. The nanoparticles can be a bio-optical probe for the target cell surface molecule. The method thereafter includes adding a nanoparticle coagulating agent to the fluid sample. The method further includes acquiring an image using dark field microscopy to detect and quantify the presence or absence of any cells in the fluid sample having the target cell surface molecule.

The nanoparticles can be dispersed in the fluid sample by vortexing. At least one fluorescent probe can be added to the fluid sample and each fluorescent probe targets a cell classification marker.

The nanoparticle coagulating agent can be a cationic polymer such as hexadimethrine bromide. The nanoparticles can be plasmonic nanoparticles detectable by dark field microscopy. The nanoparticles can be gold sols. The nanoparticles can be 10-100 nanometers in size. The nanoparticles can be conjugated with antibodies, or antibody complexes, and the antibodies can bind with specificity for cell surface antigens.

The at least one fluorescent probe can be a fluorophore.

In one non-limiting embodiment, we enumerate large mucin molecules on the surfaces of single leukocytes by light microscopy. This embodiment of the invention concerns the detection and enumeration of high molecular weight mucins on the surfaces of single cells, such as those in peripheral blood or peritoneal fluid. The purpose is to enable mucin detection in a compartment that has not been accessible for the early diagnosis, management, or treatment of cancer.

Conventional methods for detecting mucins associated with the cancer antigens CA125 (MUC16), CA 15.3 (MUC1), or CA19.9 have used peripheral blood serum as the detection compartment. There is no known functional connection between serum or peritoneal fluid levels of cancer mucins and cancer pathogenesis. In contrast, recent functional studies have indicated that MUC16 binds to peripheral blood and peritoneal fluid leukocytes, blunts anti-tumor function and alters immunophenotype. Investigation of this new compartment is limited by the detection sensitivity of state-of-the-art methods. Owing to the very large size of the previously cited mucins (order of magnitude 1-micron), a mononuclear cell will be completely covered by as few as a few hundred mucins. State-of-the-art fluorescence methods for detecting leukocyte surface bound mucins have high background levels that correspond to hundreds to thousands of mucins. It can be expected that in the early stages of disease or in late states of treatment the surface of a mononuclear cell will not be saturated by mucins and that it will be of benefit to enumerate individual bound mucins at levels well below 100 per cell which is below the limits of fluorescence detection.

The present invention uses plasmonic nanoparticles of 40 nm (0.04 micron) to 80 nm (0.08 micron) diameter and dark field microscopy to detect and enumerate individual mucins on the surface of leukocytes. This is an improvement of 100 to 1,000 fold with respect to the state-of-the-art. These plasmonic nanoparticles can be conjugated to monoclonal antibodies that are specific to the cancer antigens noted previously.

In another non-limiting embodiment, we simultaneously label single cells by fluorescent probes and plasmonic nanoparticles. This embodiment of the invention concerns detecting rare surface molecules, such as rare cell surface antigenic sites, with novel optical probes that are brighter than other, fluorescent optical probes that identify the lineage or type of cell. The purpose is to enhance light microscope performance when detecting low concentrations of surface antigens while simultaneously identifying the lineage of the cell with one or more high concentration markers. By "rare surface molecule", we mean less than 1000 surface molecules per cell.

Conventional methods use fluorescent probes both to detect rare cell surface antigenic sites and identify cell lineage or type. It is well known in the art that fluorescence excitation and emission spectral overlap from multiple lineage probes, for which there are frequently 100,000 or more binding sites for each lineage probe, will readily interfere with the approximately 100 bound probes that detect rare sites (unfavorable ratio of 1,000:1 in brightness). This interference can be minimized with complex excitation and emission filter combinations, choices of fluorescent dyes, and "color compensation" software that further minimizes the inevitability remaining spectral interferences between dyes. When there is a large, unfavorable ratio, such as that cited above, these measures are not successful.

The present invention teaches an optical probe comprising plasmonic nanoparticles that are unaffected by background light from fluorescent lineage markers. Plasmonic nanoparticles are approximately $10^5$ to $10^6$ times brighter than fluorescent probes. Consequently, in the previously cited example, the brightness of the probes that disclose rare binding sites becomes greater than the brightness of the lineage probes by ratios ranging from 100:1 up to 1,000:1 (favorable ratio of more than 100:1). This reverses the unfavorable ratio found with fluorescence and provides a 10,000-fold improvement. Methods of the invention using the optical probe can detect surface molecules at levels of 1000 or below, or at levels of 750 or below, or at levels of 500 or below, or at levels of 200 or below, or at levels of 100 or below, or at levels of 50, or at levels of 20 or below molecules per cell.

Commercially, there is a significant vested interest in maintaining usage of the hundreds of commonly used, fluorescent, lineage markers that have taken years to develop. Marketing bright plasmonic nanoparticle signals to detect rare surface antigens preserves the business for fluorescent lineage markers and introduces a heretofore-unachievable new business in detecting rare surface antigens.

In another non-limiting embodiment, the invention is a method and apparatus for suppressing background in an imaging cytometer. The invention concerns the detection and enumeration of rare antigenic sites on single cell surfaces by light microscopy. The purpose is to enhance light microscope performance when detecting low concentrations of cell surface antigen-specific optical probes in the presence of high concentrations of probes that surround a cell in its suspending medium, but are not bound to the cell.

Conventional microscopy uses fluorescent probes conjugated to antigen-specific monoclonal antibodies. It relies on the cell surface bound probes covering most of the cell and revealing it as a bright, morphologically identified, object above the light level of the free probes surrounding the cell. This method frequently requires centrifugation steps to "wash" away free probes when the background light level is too bright. This causes uncontrolled cell loss.

One may wish to use the present invention to combine the benefits of background suppression and high morphological detail in a single system for cellular analysis. Reagent suppliers for fluorescent-based probes may wish to expand their product offerings with the plasmonic nanoparticles described in this invention.

EXAMPLES

The following Examples has been presented in order to further illustrate the invention and are not intended to limit the invention in any way.

Example 1—Experimental Spectroscopy of Gold Plasmonic Nanoparticles

Figure 1A:
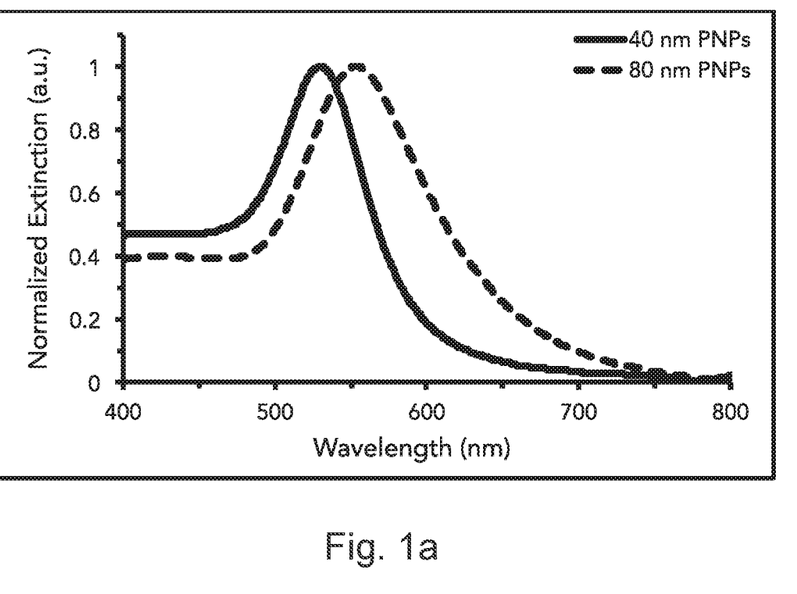
FIG. 1a shows extinction spectra of 40 nm (solid line) and 80 nm (broken line) PNPs.
Figure 1B:
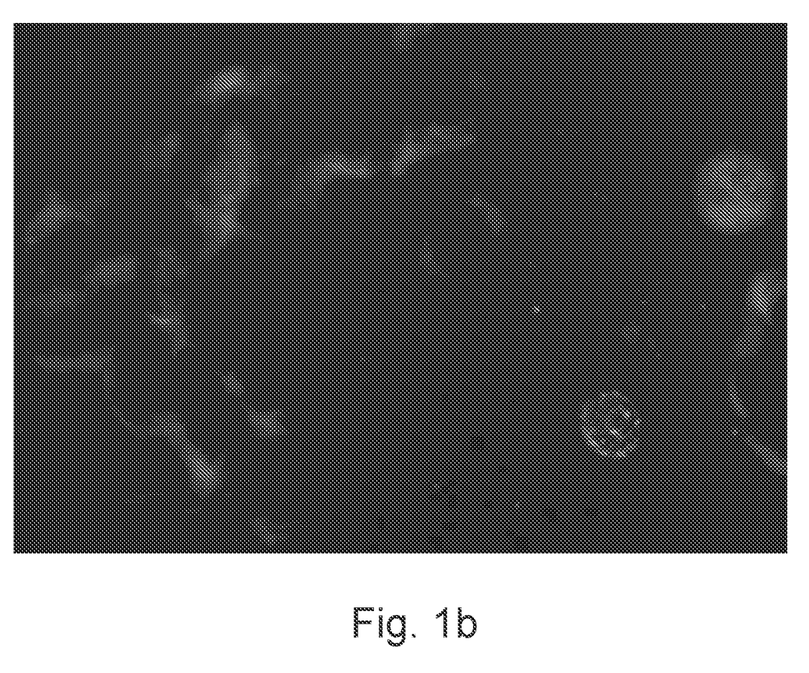
FIG. 1b shows 40 nm gold nanoparticles bound to a peripheral blood leukocyte.
Figure 1C:
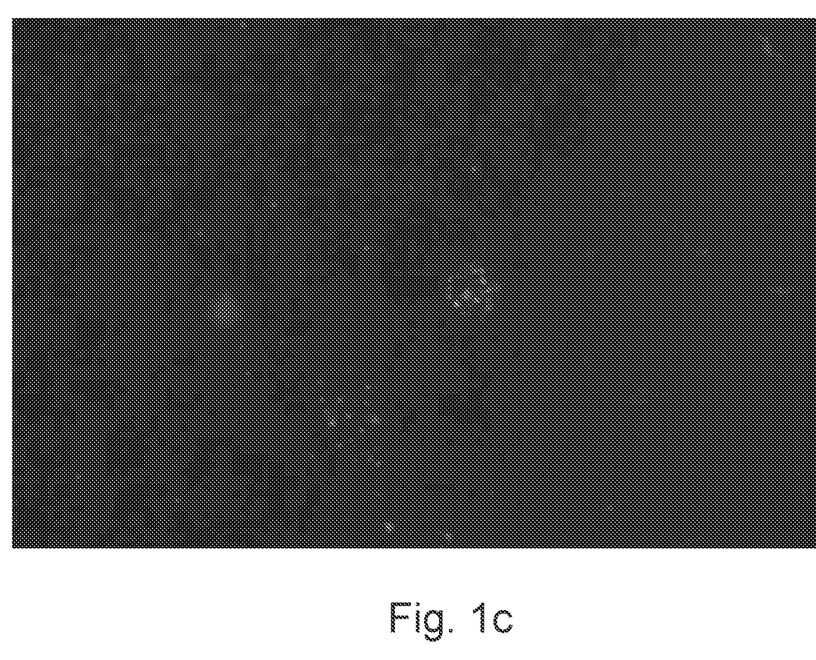
FIG. 1c shows 80 nm gold nanoparticles bound to a peripheral blood leukocyte. Note the absence of light scatter background from the cell itself compared to the image with 40 nm particles, which indicates a higher relative brightness for the 80 nm particles.

In the spectroscopy of plasmonic nanoparticles, light attenuation and light scatter have the same spectral shape. In other words, particles with an attenuation peak at 540 nm will have a light scatter peak at the same wavelength. Normalized attenuation (Extinction) spectra for two sizes of gold plasmonic nanoparticles in aqueous suspension are shown in FIG. 1a. The spectral peak wavelength for the size range 40 nm to 80 nm remains near 550 nm, which is a green wavelength, however, there is a spectral "tail" for 80 nm particles that extends into the red regions of the visible spectrum. Two dark field microscopy images illustrate cell surface binding of 40 nm and 80 nm gold nanoparticles that were conjugated with antibodies specific to peripheral blood leukocytes. The particle sizes lie well below the diffraction limit of dark field visible light microscopy, therefore the bright punctate objects seen in these images are termed the optically unresolved Airy disks corresponding to plasmonic nanoparticles or small clusters of nanoparticles. See FIGS. 1b and 1c.

Larger plasmonic nanoparticles have weaker resonance peaks but stronger geometric cross sections for light scatter (and extinction). The geometric cross section factor dominates, making the large particles "brighter" (see, Bohren et al., "Surface Modes in Small Particles in Absorption and Scattering of Light by Small Particles", Weinheim W-VVG; 2004). Thus, 80 nm gold particles are "brighter" than 40 nm particles, however particle sizes in the range 40 nm to 80 nm are sufficient for the practice of the present invention. Gold nanoparticles, such as those available from BBI Solutions Inc., Madison, Wis., are suitable for the practice of the present invention and this example.

Example 2

Deficiencies in Detecting Low Levels of Plasmonic Nanoparticle Binding by Flow Cytometry While dark field microscopy yields useful images as shown in Example 1, flow cytometry is also useful as a cellular light scatter tool. The present example illustrates the use of flow cytometry and its key limitation in solving the problem addressed by the present invention. Using the methods taught by Hansen et al. in U.S. Pat. No. 8,889,362, and "Physics of a rapid CD4 lymphocyte count with colloidal gold", *Cytometry Part A.* 2012; 81A: 222, 80 nm anti-CD4 conjugated gold nanoparticles were used with wide-angle, 630 nm, light scatter flow cytometry to label CD4+ lymphocytes. With these methods, CD4+ lymphocytes became a factor of 10 brighter than light scatter from unlabeled lymphocytes. On closer investigation of the method taught by Hansen et al. (U.S. Pat. No. 8,889,362; and "Physics of a rapid CD4 lymphocyte count with colloidal gold", *Cytometry Part A.* 2012; 81A: 222), it was found the strong wide-angle light scatter signal was produced only when the cell surface was saturated by closely packed plasmonic nanoparticles. In other words the total plasmonic nanoparticle light scatter signal from a lymphocyte was bright when the binding surface antigen was abundant and not rare.

Using a mathematical model for coherent light scattering and performing experiments at limiting dilution of monodisperse anti-CD4 PNPs, we determined that the coherent, wide-angle light scatter signal reported by Hansen et al. (U.S. Pat. No. 8,889,362; and "Physics of a rapid CD4 lymphocyte count with colloidal gold", *Cytometry Part A.* 2012; 81A: 222) was a cooperative phenomenon caused by constructive interference from regularly spaced, monodisperse particles. Reducing the packing density of bound PNPs caused the spacing between particles to become irregular; upon which the intensity of the wide-angle scatter signal dropped rapidly and nonlinearly becoming insensitive at low plasmonic nanoparticle numbers. The rapid drop in plasmonic nanoparticle light scatter signal for low abundance surface antigens was not shown by Hansen et al. (U.S. Pat. No. 8,889,362; and Hansen et al., "Physics of a rapid CD4 lymphocyte count with colloidal gold", *Cytometry Part*

A. 2012; 81A: 222) nor was the consequent disappearance of the total light scatter signal from widely spaced nanoparticles on a cell into the background light scatter from the cell itself. The present invention corrects this problem by imaging cells individually in dark field and detecting high contrast local Airy disks against the low level local (not global) light scatter background of the cell.

Example 3

Figure 2:
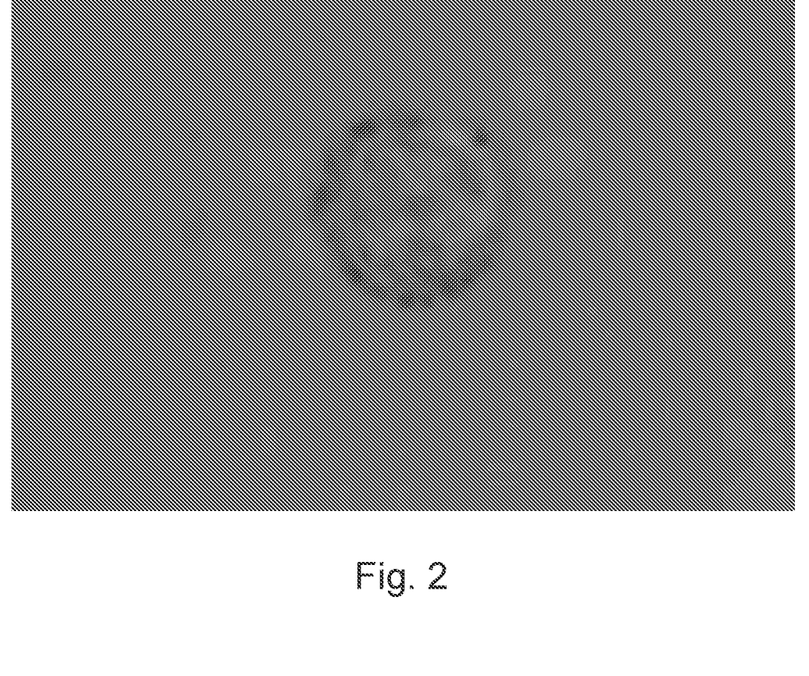
FIG. 2 shows CD4+ lymphocyte with bright field microscopy. PNP's appear as dark particles around the equatorial perimeter of the cell. Other PNP's not on the cell equator cannot be seen against the background of the cell.

Deficiencies in Detecting Plasmonic Nanoparticle Binding by Bright Field Transmission Microscopy Bright field transmission microscopy confirmed the theoretical prediction that plasmonic nanoparticles bound to the cell surface would appear as dark objects caused by intense light absorption. Anti-CD4 monoclonal antibodies were conjugated to plasmonic nanoparticles with a blue plasmonic resonance (BBI Solutions, Madison, Wis., USA). These exhibited an intense absorption maximum in the visible light range. The 60× bright field transmission image below shows a T-Helper cell partially labeled with these PNPs at limiting dilution. In this case, the PNP's are seen as intensely light absorbing objects along the outline of the cell membrane. The cell nucleus is apparent, as light absorbing background, but no PNPs can be resolved against the light absorbing background of the cell. These data confirmed that bright field transmission microscopy was not suitable and that light scatter detection by dark field microscopy would be more appropriate for PNP enumeration on leukocyte surfaces.

FIG. 2 shows CD4+ lymphocyte with bright field microscopy. PNP's appear as dark particles around the equatorial perimeter of the cell. Other PNP's not on the cell equator cannot be seen against the background of the cell.

Example 4

Figure 3:
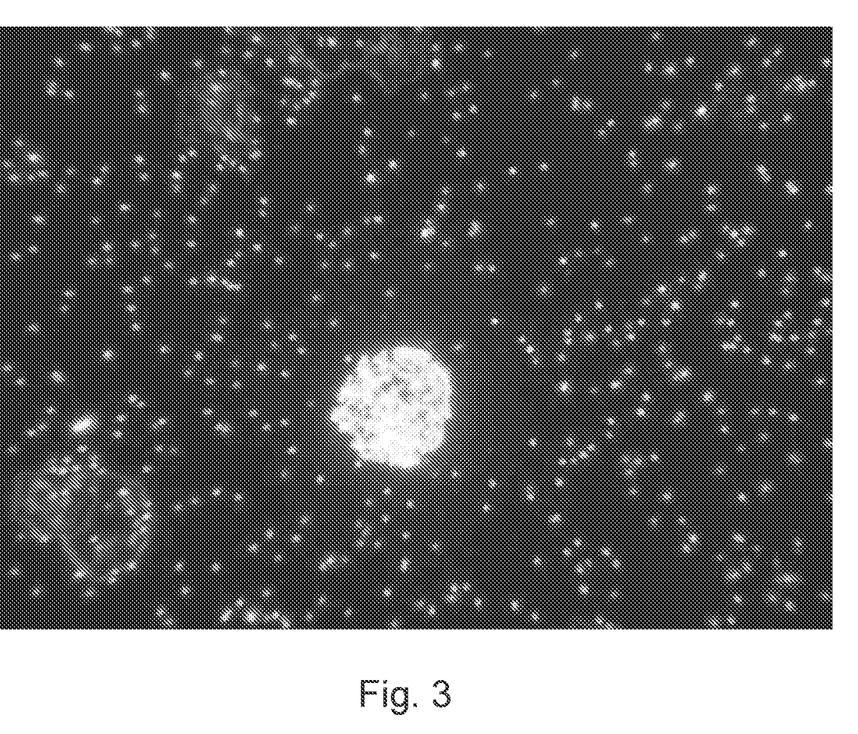
FIG. 3 shows a 60× oil immersion dark field image of a human T-Helper lymphocyte labeled with CD4 receptor specific, 80 nm PNPs. In the background are free CD4/PNPs and a few red cell "ghosts". The lymphocyte is completely covered by CD4/PNPs, and appears bright yellow.

Detecting Dense Plasmonic Nanoparticle Binding with Dark Field Transmission Microscopy Dark field transmission microscopy is sensitive to wide-angle scattered and not direct light transmission (see, J. Yguerabide and E. Eyguerabide, "Light Scattering Submicroscopic Particles as Highly Fluorescent Analogs and Their Use as tracer labels in Clinical and Biological Applications", *Analytical Biochem.* 262, 137-156, 1998). The assay methods described by Hansen et al. (U.S. Pat. No. 8,889,362; and "Physics of a rapid CD4 lymphocyte count with colloidal gold", *Cytometry Part A.* 2012; 81A: 222) were used to label T-Helper lymphocytes with 80 nm gold nanoparticles. The accompanying FIG. 3 shows a 60× oil immersion dark field image of a human T-Helper lymphocyte labeled with CD4 receptor specific, 80 nm diameter gold plasmonic nanoparticles. In the background are free CD4/PNPs and a few red cell "ghosts" remaining after red cell lysis. The lymphocyte is completely covered by anti CD4 conjugated plasmonic nanoparticles. It appears bright yellow due to the strong scattering by the plasmonic resonances of closely spaced nanoparticles. The majority of free plasmonic nanoparticles in the background are green, indicating their size (80 nm) and monomeric state. There is a sharp color difference for about 10% of free PNPs, which are yellow. Another sharp color difference is seen for about 30% of free PNPs, which are red. The sharp color changes to increasingly red-shifted wavelengths suggest the presence of free PNP aggregates that increase PNP size in a stepwise manner. These color changes are powerful tools in inferring the size of aggregates that are below the size resolution capability of visible light microscopy, which is approximately 1 micron. Aggregates of two PNPs measure only 0.16 microns and appear as spatially unresolved points of yellow scattered light. Aggregates of approximately three PNPs appear as spatially unresolved red points of scattered light. The CD4 receptors on lymphocytes are numerous (100,000 per cell) and closely packed.

Example 5

Figure 4:
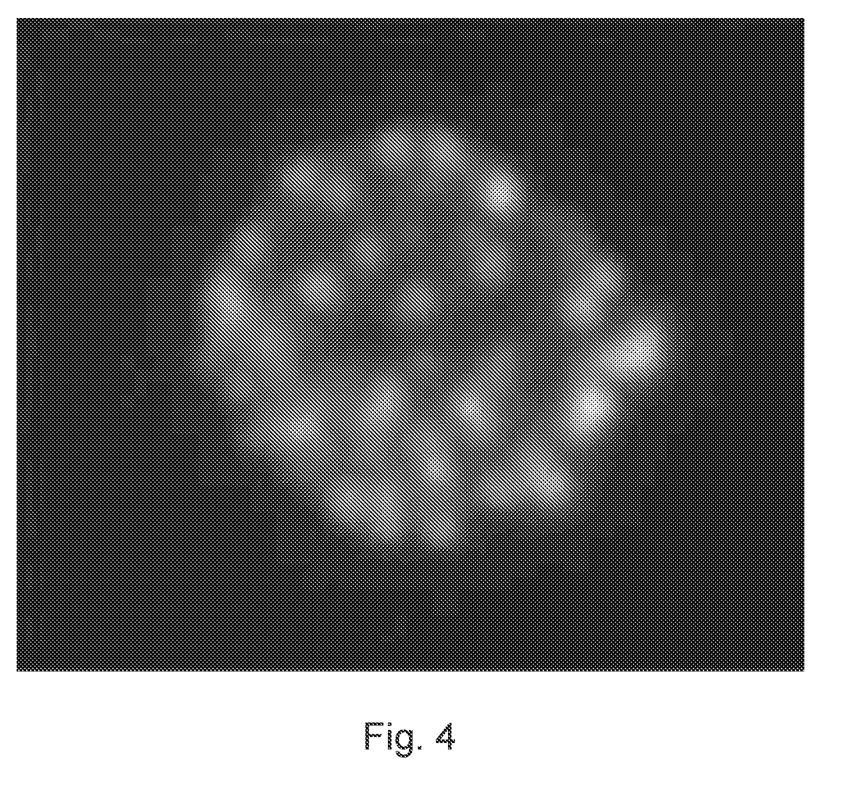
FIG. 4 shows a 60× dark field oil immersion image of a mononuclear cell labeled by 80 nm gold plasmonic nanoparticles. The image illustrates individual Airy disks caused by individual (green), pairs (yellow), and trios (red) of plasmonic nanoparticles.
Figure 4B:
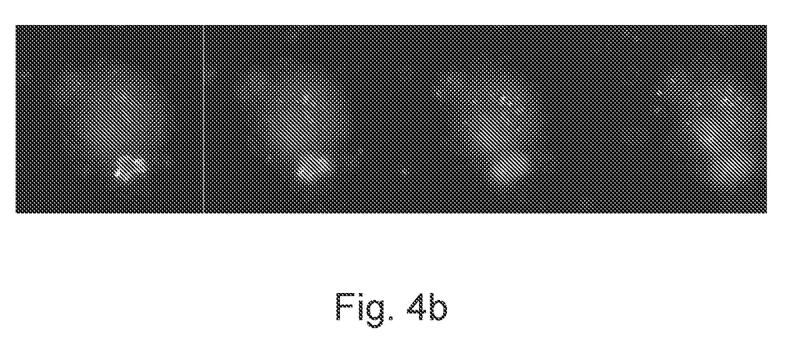
FIG. 4b shows four z-axis images taken progressively (left to right from the top of the cell to the bottom of the cell) in different focal planes using dark field microscopy at 100×. This image illustrates the fact even when only a few surface molecules bind the nanoparticle; 80 nm gold plasmonic are sufficiently bright to be resolved and enumerated through the entire volume of a leukocyte. This feature provides an advantageous tool for cell surface molecule quantification capable of interrogating the entire cell surface even when the surface molecules are not abundant. Weak fluorescence binding is frequently blocked by the interior structures of leukocytes.

Detecting Sparse Plasmonic Nanoparticle Binding with Dark Field Transmission Microscopy The accompanying 60× dark field oil immersion image (FIG. 4) is an example where plasmonic nanoparticles are not closely packed on the cell surface. The image shows a T-helper cell labeled with anti-CD4 plasmonic nanoparticle conjugates at a limiting dilution of particles that would result in fewer bound PNPs and thereby mimic the low binding to rare cell surface antigens. The bound PNPs scattered light over a range of discrete colors (green, yellow and red) indicating bound particle monomers and higher order clusters of particles. Individual plasmonic nanoparticles and clusters can be resolved. These clusters will be red-shifted in step-wise fashion, a distinct spectral feature that can also be used to detect bound PNPs. This example shows that individual plasmonic nanoparticles and plasmonic nanoparticle clusters can be identified and counted either manually or by feature recognition algorithms. Stepping the focal plane of the objective through the cell and enumerating in-focus airy disks can enumerate all plasmonic nanoparticles. See FIG. 4b.

Example 6

Figure 5A:
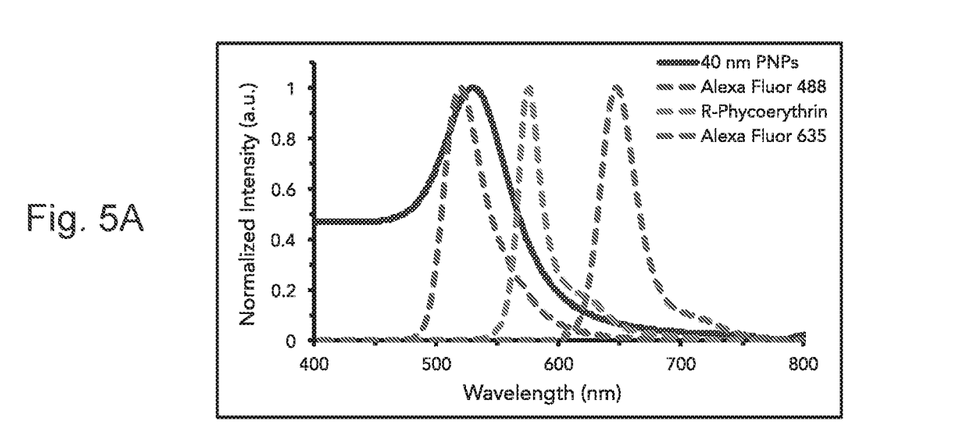
FIG. 5A shows the emission spectra for Alexa Fluor 488 and R-phycoerythrin overlap strongly with the light scatter emission from 40 nm gold nanoparticles.
Figure 5B:
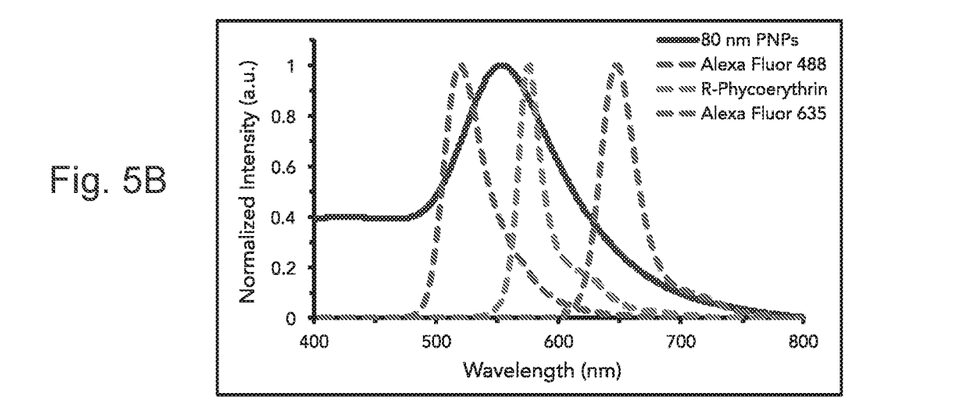
FIG. 5B shows the emission spectra for R-phycoerythrin and Alexa Fluor 635 overlap strongly with the light scatter emission from 80 nm gold nanoparticles.

Examples of Spectral Overlap of Common Fluorophores and Gold Plasmonic Nanoparticles Alexa Fluor 488, R-phycoerythrin and Alexa Fluor 635 are three examples of fluorophores that are often used simultaneously as lineage markers. Alexa Fluor 488 has an absorption maximum between 490-500 nm, an emission maximum between 510-530 nm, and an emission color of green. Alexa Fluor 635 has an absorption maximum between 630-640 nm, an emission maximum between 640-650 nm, and an emission color of far-red. The emission spectra for Alexa Fluor 488 and R-phycoerythrin overlap strongly with the light scatter emission from 40 nm gold nanoparticles in FIG. 5A. The emission spectra for R-phycoerythrin and Alexa Fluor 635 overlap strongly with the light scatter emission from 80 nm gold nanoparticles in FIG. 5B. As is demonstrated in Examples 7 and 8, the lineage marker fluorescent emission is not detectable against the plasmonic nanoparticle light scatter emission for either particle size obviating the need for color compensation even in the extreme case where the plasmonic nanoparticle light scatter signal has essentially the same spectral content as the signal from lineage markers.

Example 7

Resolving Low Level Plasmonic Nanoparticle Binding in the Presence of an Overlapping Alexa Fluor 488 Fluorescent Lineage Marker The following procedure was used to create dark field and fluorescence images of human patient peripheral blood monocytes bearing MUC16 surface bound mucins. The sample was simultaneously labeled by 80 nm anti CA125 gold nanoparticles and Alexa Fluor 488 conjugated an anti-CD14 lineage marker:

1. Place 50 μL of fresh blood in microcentrifuge tube.
2. Add 5 μL of anti-CD14 Alexa Fluor 488 antibody to fresh blood.
3. Incubate blood @ RT in the dark for 30 min.
4. Wash blood 1× with PBS (centrifuge settings: 250 g for 5 min).
5. Add 3.2 μL of anti-CA125-PNPs (stock OD≈53.2, stock conc. (nM)≈0.77) and mix by vortexing.
6. Add 4 μL of hexadimethrine bromide (SigmaAldrich) and mix by vortexing.
7. Place 6 μL of labeled blood on glass slide.
8. Seal with coverslip and nail polish.
9. Image using dark-field & wide-field fluorescence microscope using 100×/1.35 oil objective & 1.2-1.4 DF condenser and FITC filter set.

Figure 6A:
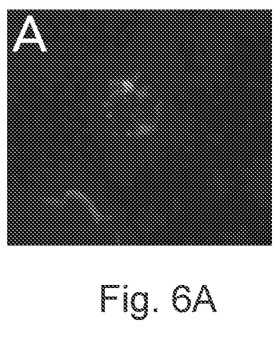
FIG. 6A shows immune bound CA125 detection with anti-CA125-PNPs. 100× dark-field oil immersion image of anti-CA125-PNPs bound to a white blood cell.
Figure 6B:
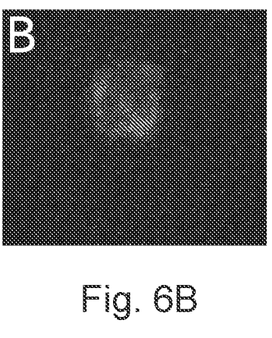
FIG. 6B shows immune bound CA125 detection with anti-CA125-PNPs. Wide-field fluorescence image a monocyte stained with anti-CD14 Alexa Fluor 488.

FIG. 6A is a typical narrow depth of field (~1 micron) dark field image of the equatorial plane of a cell with punctate bright Airy disks caused by bound plasmonic nanoparticles on the surface. An isotype control experiment was also carried out using the same procedure but using anti biotin conjugated 80 nm plasmonic nanoparticles. No biotin is expected to be present on the surface of monocytes. The particle enumerations showed no more than 2 Airy disks on any monocyte, and most frequently the count was zero, which indicated that the anti CA125 binding was specific. FIG. 6B is the fluorescent image of the same cell as in FIG. 6A, showing it to be a monocyte by the lineage marker Alexa Fluor 488 anti CD14. The combined results from the specific probe and the isotype control suggest a very low level of approximately 20 MUC16 molecules per monocyte were detected in this experiment. This example also demonstrates minimal fluorescent dye quenching by the plasmonic nanoparticles.

Example 8

Resolving Low Level Plasmonic Nanoparticle Binding in the Presence of an Overlapping Phycoerythrin Fluorescent Lineage Marker The following procedure was used to create dark field and fluorescence images of human patient peripheral blood monocytes bearing CD4 surface receptors. The sample was simultaneously labeled by 80 nm anti CD4 gold nanoparticles at low affinity to simulate low abundance binding, and an R-Phycoerythrin conjugated anti-CD45 lineage marker:

EXPERIMENTAL DETAILS

1. Place 50 μL of fresh blood in microcentrifuge tube.
2. Add 5 μL of anti-CD45-PE antibody to fresh blood.
3. Incubate blood @ RT in the dark for 30 min.
4. Wash blood 1× with PBS (centrifuge settings: 250 g for 5 min).
5. Add 2 μL of anti-CD4-PNPs (stock OD≈147.2, stock conc. (nM)≈2.13) and mix by vortexing.
6. Add 4 μL of hexadimethrine bromide and mix by vortexing.
7. Place 6 μL of labeled blood on glass slide.
8. Seal with coverslip and nail polish.
9. Image using dark-field & wide-field fluorescence microscope using 100×/1.35 oil objective & 1.2-1.4 DF condenser and PE filter set.

Figure 7A:
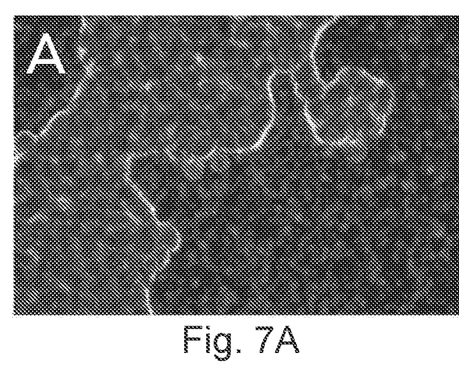
FIG. 7A shows co-labeling of 80 nm immune conjugated PNPs and a spectrally overlapping fluorescent lineage marker. A 100× dark-field oil immersion image of low affinity anti-CD4 immune conjugated gold plasmonic nanoparticles chosen to create low level binding. No quenching is observed when performing co-labeling procedures.
Figure 7B:
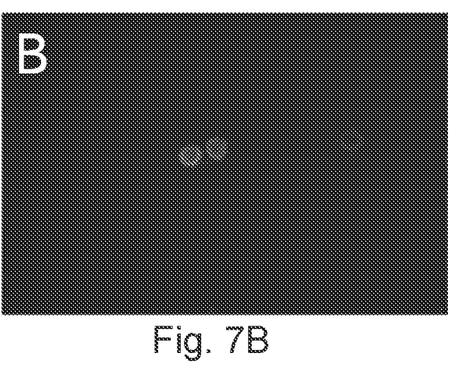
FIG. 7B shows co-labeling of 80 nm immune conjugated PNPs and a spectrally overlapping fluorescent lineage marker. A wide-field fluorescent image of WBCs labeled with anti-CD45-PE fluorophores. No quenching is observed when performing co-labeling procedures.

FIG. 7B is the fluorescent image of the same cell as in FIG. 7A, showing it to be a leukocyte by the lineage marker R-Phycoerythrin anti-CD45. This example demonstrates the absence of lineage marker background fluorescence in the dark field light scatter image of plasmonic nanoparticle labeling. This example also demonstrates minimal fluorescent dye quenching by the plasmonic nanoparticles.

Thus, the invention provides a method for detecting a target cell surface molecule and classifying cell types in a fluid sample. The method involves the addition of a reagent to the fluid sample. The reagent includes nanoparticles with visible light plasmonic resonances, and at least one fluorescent probe. The nanoparticles are a bio-optical probe for the target cell surface molecule. Each fluorescent probe targets a cell classification marker. The method further involves the acquisition of an image using dark field microscopy and fluorescence microscopy to detect and quantify the presence or absence of any cells in the fluid sample having the target cell surface molecule or having the cell classification marker and quantifying the target cell surface molecule on a cell-by-cell basis.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A method for classifying cell types in a fluid sample, detecting and quantifying a target cell surface molecule on said classified cell types, the method comprising:
   (a) adding a reagent to the fluid sample, the reagent comprising (i) nanoparticles with optical plasmonic resonances and wherein the nanoparticles are plasmonic nanoparticles detectable by dark field microscopy and (ii) at least one fluorescent probe and wherein the at least one fluorescent probe is detectable by fluorescence microscopy, wherein the nanoparticles are a bio-optical probe for the target cell surface molecule, and wherein each fluorescent probe targets a cell classification marker;
   (b) acquiring an image using dark field microscopy and fluorescence microscopy to detect and quantify the presence of the target cell surface molecule, on a cell-by-cell basis for any cells in the fluid sample having the cell classification marker.
2. The method of claim 1 wherein:
   the target cell is a leukocyte.
3. The method of claim 1 wherein:
   the target cell surface molecule is a rare cell surface antigen.
4. The method of claim 1 wherein:
   the target cell surface molecule is the mucin molecule MUC16.
5. The method of claim 1 wherein:
   the nanoparticles are gold sols.
6. The method of claim 1 wherein:
   the nanoparticles are 10-200 nanometers in size.
7. The method of claim 1 wherein:
   the nanoparticles are 10-100 nanometers in size.
8. The method of claim 1 wherein:
   the nanoparticles are 40-80 nanometers in size.

9. The method of claim 1 wherein:
the nanoparticles are conjugated with antibodies, or antibody complexes and the antibodies bind with specificity for cell surface antigens.

10. The method of claim 1 wherein:
the at least one fluorescent probe is a fluorophore.

11. The method of claim 1 wherein:
the at least one fluorescent probe has an absorption maximum between 490-500 nm, an emission maximum between 510-530 nm, and an emission color of green.

12. The method of claim 1 wherein:
the at least one fluorescent probe is R-phycoerythrin.

13. The method of claim 1 wherein:
the at least one fluorescent probe has an absorption maximum between 630-640 nm, an emission maximum between 640-650 nm, and an emission color of far-red.

14. The method of claim 1 wherein:
the nanoparticles create intense light scatter based spectral radiance per unit area, the intense light scatter based spectral radiance exceeding the spectral radiance of a fluorophore by $10^5$ to $10^6$.

15. The method of claim 1 wherein step (b) comprises:
the at least one fluorescent probe has a fluorescence emission one or more orders of magnitude weaker than that caused by the nanoparticles light scatter thereby not interfering with the nanoparticle light scatter.

16. The method of claim 1 wherein:
the nanoparticles appear as spatially punctate, intense light sources in the acquired image, and
the punctate light sources appearing as individual Airy discs of intense light emission in the acquired image such that the Airy discs are readily detectable in the acquired image.

17. The method of claim 1 wherein:
the nanoparticles are coated with protein spacers, the protein spacers providing a physical spacer of 1 to 100 nanometers that prevents the approach of fluorophores and avoids fluorescence quenching.

18. The method of claim 17 wherein:
the protein spacers comprise IgG antibodies.

19. The method of claim 1 wherein:
detection and quantification of the target cell surface molecule and detection of the presence or absence of any cells in the fluid sample having the cell classification marker can be done manually.

20. The method of claim 1 wherein:
detection and quantification of the target cell surface molecule and detection of the presence or absence of any cells in the fluid sample having the cell classification marker can be done using automated image analysis methods.

21. The method of claim 1 wherein step (b) comprises:
stepping a focal plane of an objective of a dark field microscope through at least one labeled cell in the fluid sample having the target cell surface molecule and enumerating in-focus plasmonic nanoparticles on the least one labeled cell.

22. The method of claim 1 wherein step (b) comprises:
acquiring a dark field microscopy image.

23. The method of claim 1 wherein step (b) comprises:
acquiring an image using flow cytometry.

24. A reagent for detecting a target cell surface molecule and classifying cell types in a fluid sample, the reagent comprising:
nanoparticles with optical plasmonic resonances and wherein the nanoparticles are plasmonic nanoparticles detectable by dark field microscopy, wherein the nanoparticles are a bio-optical probe for the target cell surface molecule; and
at least one fluorescent probe, wherein each fluorescent probe targets a cell classification marker, and wherein the at least one fluorescent probe is detectably by fluorescence microscopy.

25. The reagent of claim 24 wherein:
the nanoparticles are gold sols.

26. The reagent of claim 24 wherein:
the nanoparticles are 10-200 nanometers in size.

27. The reagent of claim 24 wherein:
the nanoparticles are 10-100 nanometers in size.

28. The reagent of claim 24 wherein:
the nanoparticles are 40-80 nanometers in size.

29. The reagent of claim 24 wherein:
the nanoparticles are conjugated with antibodies, and
the antibodies bind with specificity for cell surface antigens.

30. The reagent of claim 24 wherein:
the at least one fluorescent probe is a fluorophore.

31. The reagent of claim 24 wherein:
the at least one fluorescent probe has an absorption maximum between 490-500 nm, an emission maximum between 510-530 nm, and an emission color of green.

32. The reagent of claim 24 wherein:
the at least one fluorescent probe is R-phycoerythrin.

33. The reagent of claim 24 wherein:
the at least one fluorescent probe has an absorption maximum between 630-640 nm, an emission maximum between 640-650 nm, and an emission color of far-red.

34. A method for classifying cell types in a fluid sample, detecting and quantifying a target cell surface molecule on said classified cell types, the method comprising:
(a) adding a reagent to the fluid sample, the reagent comprising (i) nanoparticles with optical plasmonic resonances and wherein the nanoparticles are plasmonic nanoparticles detectable by scattered light microscopy and (ii) at least one fluorescent probe and wherein the at least one fluorescent probe is detectable by fluorescence microscopy, wherein the nanoparticles are a bio-optical probe for the target cell surface molecule, and wherein each fluorescent probe targets a cell classification marker;
(b) acquiring an image using scattered light microscopy and fluorescence microscopy to detect and quantify the presence of the target cell surface molecule, on a cell-by-cell basis for any cells in the fluid sample having the cell classification marker.

\* \* \* \* \*